(12) United States Patent
Nobuyoshi et al.

(10) Patent No.: US 6,447,479 B1
(45) Date of Patent: Sep. 10, 2002

(54) BLOOD VESSEL DILATATION APPARATUS

(75) Inventors: Masakiyo Nobuyoshi, Kitakyushu; Yoshikazu Takahashi, Nakai-machi; Shigeyuki Mineo; Kenichi Kumoyama, both of Fujinomiya, all of (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/414,441

(22) Filed: Oct. 7, 1999

(30) Foreign Application Priority Data

Oct. 8, 1998 (JP) .......................................... 10-286119

(51) Int. Cl.[7] .......................................... A61M 29/00
(52) U.S. Cl. ..................... 604/96.01; 606/194; 604/921
(58) Field of Search ............................... 604/96.01, 103, 604/103.04, 103.09, 103.1, 103.14; 606/915, 921, 192, 194

(56) References Cited

U.S. PATENT DOCUMENTS

| | | | |
|---|---|---|---|
| 5,032,113 A | | 7/1991 | Burns |
| 5,047,045 A | * | 9/1991 | Arney et al. |
| 5,176,637 A | | 1/1993 | Sagae |
| 5,423,754 A | * | 6/1995 | Cornelius et al. ........... 604/103 |
| 5,549,552 A | * | 8/1996 | Peters et al. ............. 604/96.01 |
| 5,554,121 A | * | 9/1996 | Ainsworth et al. ....... 604/96.01 |
| 5,759,191 A | | 6/1998 | Barbere |
| 5,868,706 A | * | 2/1999 | Cox ......................... 604/96.01 |

FOREIGN PATENT DOCUMENTS

| | | |
|---|---|---|
| EP | 0 452 901 | 10/1991 |
| EP | 0 850 659 | 7/1998 |

* cited by examiner

Primary Examiner—Angela D. Sykes
Assistant Examiner—Loan H. Thanh
(74) Attorney, Agent, or Firm—Burns, Doane, Swecker & Mathis, LLP

(57) ABSTRACT

A blood vessel dilatation apparatus includes an inner tube having a lumen; an outer tube forming a lumen between the outer tube and an outer surface of the inner tube; a dilatation member; a first opening provided at a rear end portion of the inner tube and communicating with the lumen; a second opening provided at a rear end portion of the outer tube and communicating with the lumen. The outer tube includes a front-side tube and a rear-side tube fixed to the front-side tube. The front-side tube has a diameter changing portion whose outer and inner diameters decrease toward its front end. A front portion of the rear-side tube is connected with an inner surface of a rear end portion of the front-side tube. An inner surface of the front portion of the rear-side tube is connected with the inner tube.

22 Claims, 10 Drawing Sheets

BLOOD VESSEL DILATATION APPARATUS

BACKGROUND OF THE INVENTION

The present invention relates to a blood vessel dilatation apparatus for restoring the blood stream at a peripheral side of a stenotic portion by dilating it in treating stenosis of a blood vessel. In other words, the present invention relates to a blood dilatation catheter.

It has become possible that an apparatus of Percutaneous Transluminal Coronary Angioplasty (hereinafter referred to as PTCA dilatation catheter) that is used to treat myocardial infarction or angina pectoris into a fine blood vessel or a:complicated lesion portion. This is because a PTCA dilatation catheter having a small diameter and flexible has been developed. The PTCA dilatation catheter has a lumen through which a guide wire is passed. In inserting PTCA dilatation catheter into a blood vessel, it is operated together with the guide wire.

A catheter tube constituting the PTCA dilatation catheter requires at least two lumens: One is used to insert the guide wire therethrough, and the other is used as a path through which an operating fluid for dilating and contracting a dilatation member (balloon) for dilating a stenotic portion of a blood vessel. Thus, heretofore, an uncoaxial porous plastic tube having two uncoaxial lumens or a plastic catheter tube having coaxial inner and outer tubes is used.

The PTCA dilatation catheter having the above-described uncoaxial catheter tube has a characteristic that it can be smoothly pressed into a blood vessel. But the operability of the guide wire is poor. Further, it is not suitable for reducing the diameter of the catheter tube. Therefore, in recent years, the above-described plastic tube having coaxial inner and outer tubes is mainly used.

In dilating the a stenotic portion of a blood vessel, the guide wire is inserted into the stenotic portion and then the dilatation member located at the front end of the blood vessel dilatation catheter is inserted into the stenotic portion. Accordingly, it is preferable that the front side of the blood vessel dilatation catheter is flexible to follow the movement of the guide wire. It is also preferable that the blood vessel dilatation catheter is small (low profile) to allow the dilatation member to arrive at the stenotic portion situated at a peripheral blood vessel. It is also preferable that the rear portion of the blood vessel dilatation catheter located outside proximally from the stenotic portion-present peripheral blood vessel is thicker than the front portion of the blood vessel dilatation catheter to allow the catheter to be smoothly pressed in the blood vessel and secure torque transmittable performance.

To this end, in the above-described plastic tube having the coaxial inner and outer tubes, the diameter of the outer tube is decreased in one stage or a multistage toward the front end of the catheter at a portion a predetermined length rearward from the front end of the catheter. In this construction, the inner diameter of the front end portion of the outer tube is necessarily small. It is preferable that the inner diameter of the rear portion of the outer tube is larger than that of the front end portion thereof to allow smooth flow of the operating fluid for dilating and contracting the dilatation member.

However, in the above-described construction, the inner diameter of the outer tube is large in the rear portion of the catheter. Thus, the clearance between the inner surface of the outer tube and the inner tube is necessarily large. Consequently, at a position corresponding to the rear end portion of the catheter (outer tube), the inner tube may be bent, curved or twisted inside the outer tube when the catheter passes a curved portion of the blood vessel. As a result, the operating fluid for dilating and contracting the dilatation member is prevented from smoothly flowing between the inner tube and the outer tube, which means that it takes long to dilate and contract the dilatation member. Further, a pressing force generated at the rear portion of the catheter is absorbed by intermediate parts thereof and thus cannot be reliably transmitted to the front end thereof.

Therefore, it is an object of the present invention to provide a blood vessel dilatation apparatus which can arrive preferably at a stenotic portion located in a peripheral blood vessel; which can be pressed favorably in the blood vessel (travel performance in blood vessel); which does not intercept a duct of a dilatation member or prevents a liquid from flowing into the dilatation member; and which allows the dilatation member to dilate and contract for a short period of time (preferable in response performance in dilatation and contraction).

It is another object of the present invention to provide a blood vessel dilatation apparatus, of a coaxial construction, which has an inner tube and an outer tube having a small inner diameter at its front portion and a comparatively large inner diameter at its rear portion and which prevents the inner tube disposed inside the outer tube from being bent, curved or twisted.

SUMMARY OF THE INVENTION

The object of this invention is to provide a blood vessel dilatation apparatus comprising: an inner tube having a first lumen whose a distal end is open; an outer tube coaxial with said inner tube, having a front end at a position rearward in a predetermined length from said front end of said inner tube, and forming a second lumen between said outer tube and an outer surface of said inner tube; a dilatation member contractible or foldable, having a front end portion secured to said inner tube and a rear end portion secured to said outer tube and communicating with said second lumen in the vicinity of a rear end thereof; a first opening provided at a rear end portion of said inner tube and communicating with said first lumen; and a second opening provided at a rear end portion of said outer tube and communicating with said second lumen, wherein said outer tube has a front part having a comparatively small diameter and located rearward in a predetermined length from a position at which said outer tube and said dilatation member are connected with each other; and a rear part having an inner diameter greater than that of said front part at least in a greater part thereof; and said outer tube is fixed to said inner tube through an inner surface of said rear part.

DETAILED DESCRIPTION OF THE PREFERRED EMBODIMENTS

Figure 1:
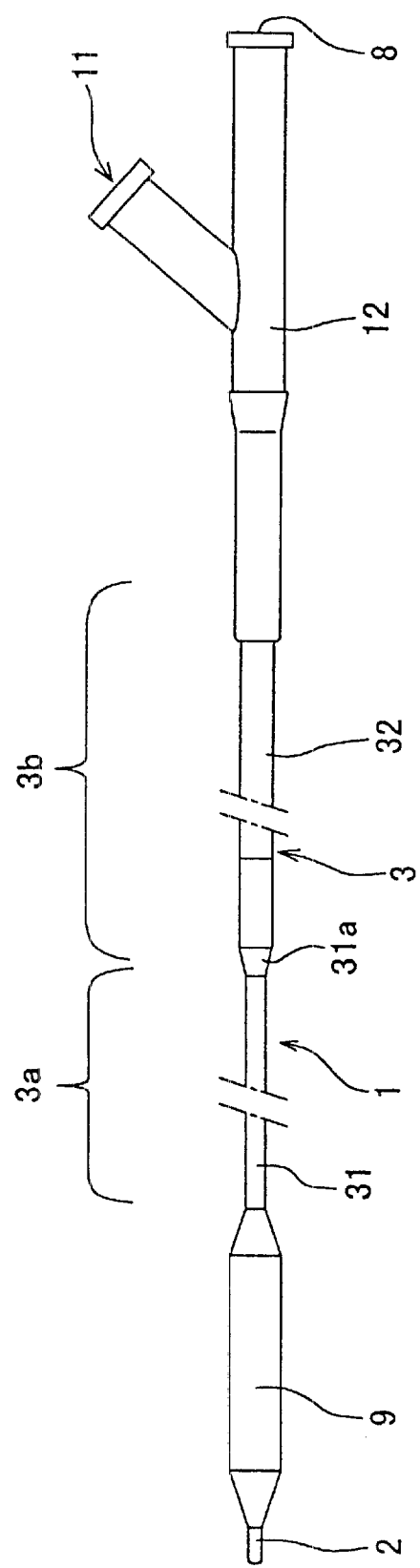
FIG. 1 shows an embodiment of the blood vessel dilatation apparatus of the present invention.

The blood vessel dilatation apparatus of the present invention will be described below with reference to the drawings.

A blood vessel dilatation apparatus 1 of the present invention (blood vessel dilatation catheter) includes an inner tube 2 having a first lumen 5 whose a distal end is open ; an outer tube 3 coaxial with the inner tube 2, having a front end at a position rearward in a predetermined length from the front end of the inner tube 2, and forming a second lumen 6 between the outer tube 3 and an outer surface of the inner tube 2; a contractible or foldable dilatation member 9 having a front end portion secured on the inner tube 2 and a rear end portion secured on the outer tube 3, and communicating with the second lumen 6 in the vicinity of the rear end thereof; a first opening 8 provided at a tear end portion of the inner tube 2 and communicating with the first lumen 5; and a second opening 11 provided at a rear end portion of the outer tube 3 and communicating with the second lumen 6. The outer tuber 3 has a front part 3a having a comparatively small inner diameter and located rearward in a predetermined length from a position at which the outer tube 3 and the dilatation member 9 are connected with each other; and a rear part 3b having an inner diameter greater than that of the front part 3a in a greater part thereof. The outer tube 3 is fixed to the inner tube 2 through an inner surface of the rear part 3b. The blood vessel dilatation apparatus 1 of the present invention has a fixed portion fixing the inner tube to the outer tube at a front end portion of the rear part 3b.

The blood vessel dilatation apparatus 1 will be described below with reference to the drawings.

As shown in FIG. 1, the blood vessel dilatation apparatus 1 includes a body having an inner tube 2, an outer tube 3, and a dilatation member 9; and a branch hub 12.

The inner tube 2 has a first lumen 5 whose front end is open. The first lumen 5 is provided to insert a guide wire therethrough and communicates with a first opening 8 forming a guide wire port provided on a branch hub 12 which will be described later. The diameter of a front portion of the inner tube 2 may be decreased toward its front end in one stage or a multi-stage to facilitate the insertion of the blood vessel dilatation apparatus 1 into a blood vessel.

The following materials can be preferably used to form the inner tube 2; polyolefin (for example, polyethylene, polypropylene, ethylene-propylene copolymer, ionomer, and a mixture containing two or more thereof); crosslinked polyolefins; high polymer materials including polyvinyl chloride, polyamide, polyamide elastomer, polyester, polyester elastomer, polyurethane, polyurethane elastomer, polyimide, fluoroplastics; and plastic materials such as silicone rubber, latex rubber, and the like. The length of the inner tube 2 is 300–2000 mm, and favorably, 500–1600mm. The outer diameter thereof is 0.1 mm–1.0 mm, and favorably, 0.3–0.7 mm. The thickness thereof is 10–150 $\mu$m, and favorably 20–100 $\mu$m.

The inner tube 2 is inserted into the outer tube 3 in such a manner that the front end of the inner tube 2 projects forward from the outer tube 3. A second lumen 6 is formed of the outer surface of the inner tube 2 and the inner surface of the outer tube 3 such that the second lumen 6 extends over the whole length of the outer tube 3. The second lumen 6 has a sufficient volume.

In the embodiment, the outer tube 3 includes a front-side tube 31 and a rear-side tube 32 whose front portion 32a is joined with the rear end portion of the front-side tube 31. A branch hub 12 is fixed to the rear end of the rear-side tube 32 (outer tube 3). The outer tube 3 includes the front-side tube 31 and the rear-side tube 32 fixed to the front-side tube 31. The front portion 32a of the rear-side tube 32 is connected with (fixed to) the inner surface of the rear end portion of the front-side tube 31. The inner surface of the front portion 32a of the rear-side tube 32 is connected with (fixed to) the inner tube 2.

Figure 5:
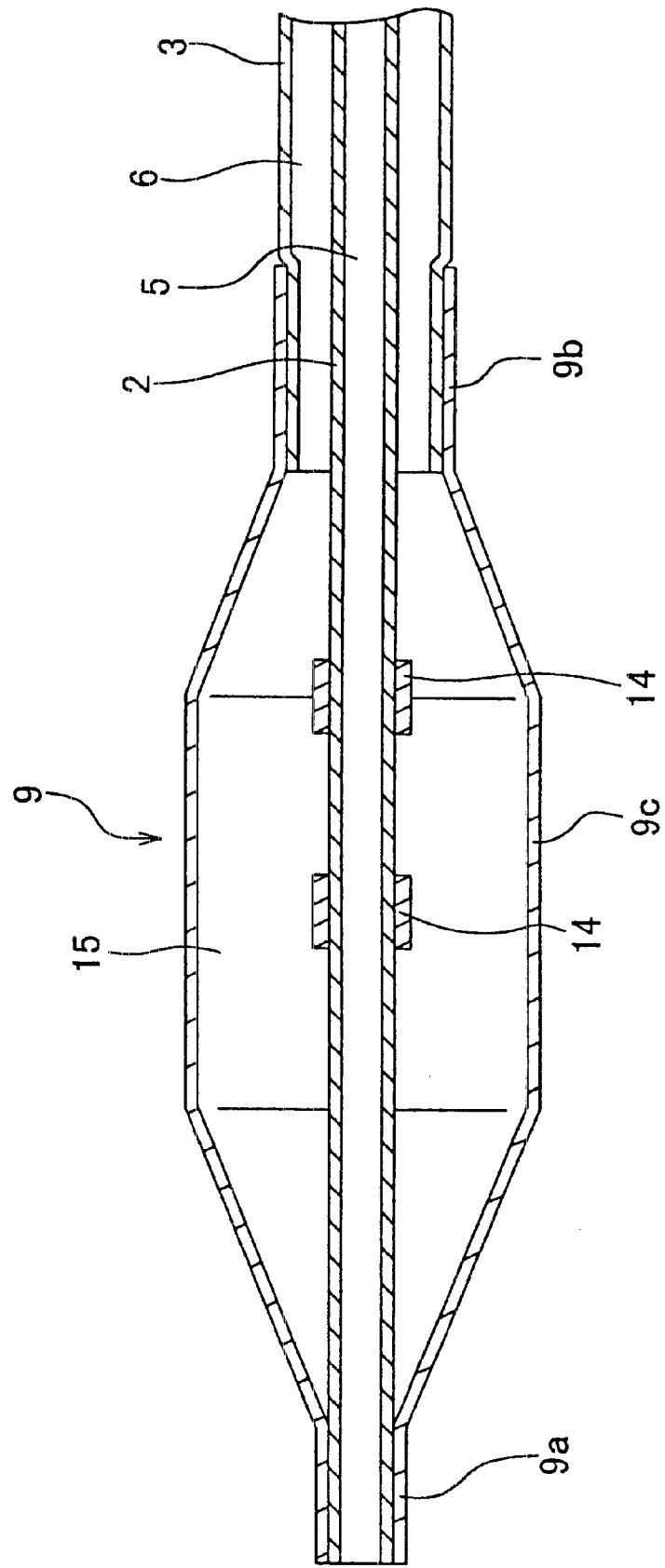
FIG. 5 is an enlarged vertical section showing the construction of a front part of the blood vessel dilatation apparatus shown in FIG. 1.

As shown in FIG. 5, the front end of the outer tube 3, namely, the front end of the front-side tube 31 is located rearward at a predetermined distance from the front end of the inner tube 2. The front end of the outer tube 3 (front-side tube 31) is joined with the dilatation member 9.

Figure 3:
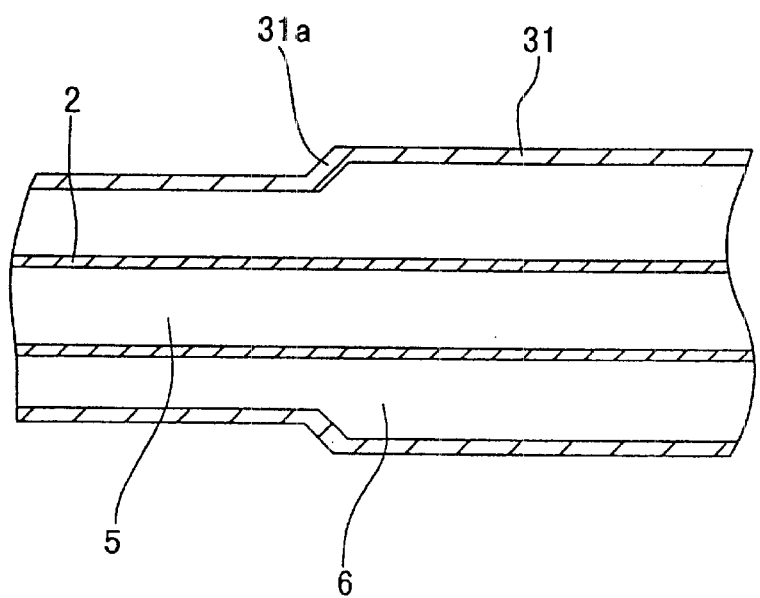
FIG. 3 is an enlarged vertical section showing the construction of the vicinity of a diameter changing portion of the blood vessel dilatation apparatus shown in FIG. 1.

As shown in FIG. 3, the front-side tube 31 has a diameter changing portion (in other words, a taper portion or small-diameter portion) 31a at a portion located between its front and rear ends. The diameter changing portion (in other words, a taper portion or small-diameter portion) 31a is provided on the front side from the fixed portion. In other words, the fixed portion is located on the rear side from the diameter changing portion (tapes portion) 31a. The outer and inner diameters of the diameter changing portion 31a decrease to its front end. More specifically, the diameter changing portion 31a is tapered to its front end. That is, the outer and inner diameters of the diameter changing portion 31a change gradually. The outer diameter of the front-side tube 31 positioned forward from the diameter changing portion 31a is smaller than the outer diameter thereof positioned rearward from the diameter changing portion 31a. Similarly, the inner diameter of the front-side tube 31 positioned forward from the diameter changing portion 31a is smaller than the inner diameter thereof positioned rearward from the diameter changing portion 31a.

Owing to the above construction of the front-side tube 31, the front portion of the portion of the blood vessel dilatation apparatus (body) has a diameter changing. Thus, the blood vessel dilatation apparatus can be inserted into a distal blood vessel. Because the front portion of the blood vessel dilatation apparatus is, made of a high polymer material, it is sufficiently flexible.

In the example shown in FIG. 3, owing to the formation of the diameter changing portion 31a, the diameter of the front side of the outer tube 3 decreases in one stage. But two or diameter changing portions may be formed to decrease the diameter of the front side of the outer tube 3 in a multi-stage.

In this embodiment, as shown in FIG. 5, the inner and outer diameters of the front end of the front part 3a (front portion of front-side tube 31) of the outer tube 3 connected with the dilatation member 9 are smaller than those of the outer tube 3 at its rear side. By reducing the outer diameter of the front end of the front part 3a, it is possible to reduce the difference in level between the rear end portion of the dilatation member 9 and the outer surface of the outer tube 3.

Such an outer tube having different diameters can be formed by connecting front and rear portions of an outer tube prepared separately with each other, by fabrication such as draw-down or by extrusion molding such that the diameter of the front side is smaller than that of the body side.

Figure 2:
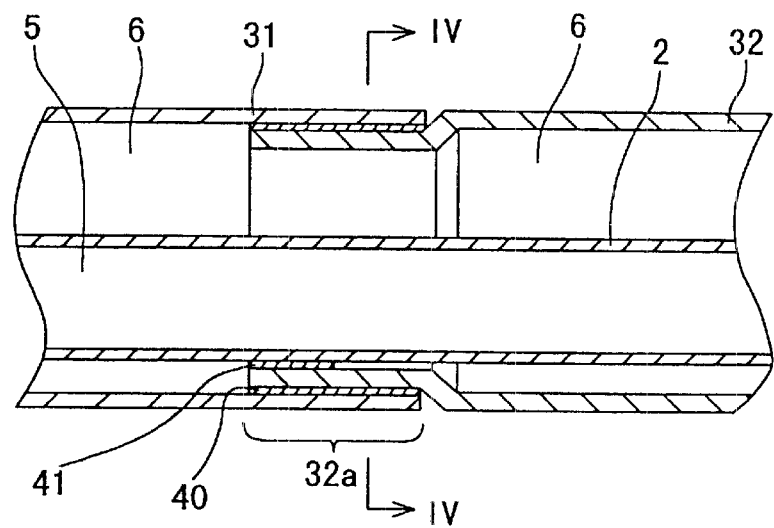
FIG. 2 is an enlarged vertical section showing the construction of a fixed portion of inner and outer tubes of the blood vessel dilatation apparatus shown in FIG. 1.

As shown in FIG. 1, except the front portion 32a, the rear-side tube 32 has substantially the same outer diameter over its whole length, and at least except the front portion 32a, the inner diameter of the rear-side tube 32 is set larger than the inner diameter of the front-side tube 31. As shown in FIG. 2, the inner diameter of the front portion 32a of the rear-side tube 32 is smaller than that of the rear part of the rear-side tube 32. The outer diameter of the front portion 32a is substantially equal to the inner diameter of the rear portion of the front-side tube 31. The front portion 32a is joined with the inner surface of the rear portion of the front-side tube 31. The-inner surface of the front portion 32a is joined with (fixed to) the inner tube 2.

In the embodiment, the outer tube 3 has the front part 3a having a comparatively small inner diameter and located in a predetermined length forward from the diameter changing portion 31a of the front-side tube 31 to the position of connection between the dilatation member 9 and the outer tube 3. The rear part 3b of the outer tube 3 is formed of the front-side tube 31 in the range between the diameter changing portion 31a and the rear end thereof and the rear-side tube 32. The inner diameter of the rear part 3b is greater than that of the front part 3a in the greater part thereof. Therefore, the clearance between the inner surface of the outer tube 3 and the outer surface of the inner tube 2 in the rear part 3b is greater than that between the inner surface of the outer tube 3 and the outer surface of the inner tube 2 in the front part 3a in the greater part thereof.

As the construction of the above-described "The inner diameter of the rear part 3b is greater than that of the front part 3a in the greater part thereof", the following two constructions are exemplified:

(1) The inner diameter of the rear part 3b is greater than that of the front part 3a over the whole length of the rear part 3b.

(2) The inner diameter of the rear part 3b is greater than that of the front part 3a in the greater part thereof except one or several portions in which the inner diameter of the rear part 3b is equal to or smaller (for example, the diameter changing front portion 32a of the rear-side tube 32) than that of the front part 3a.

Figure 4:
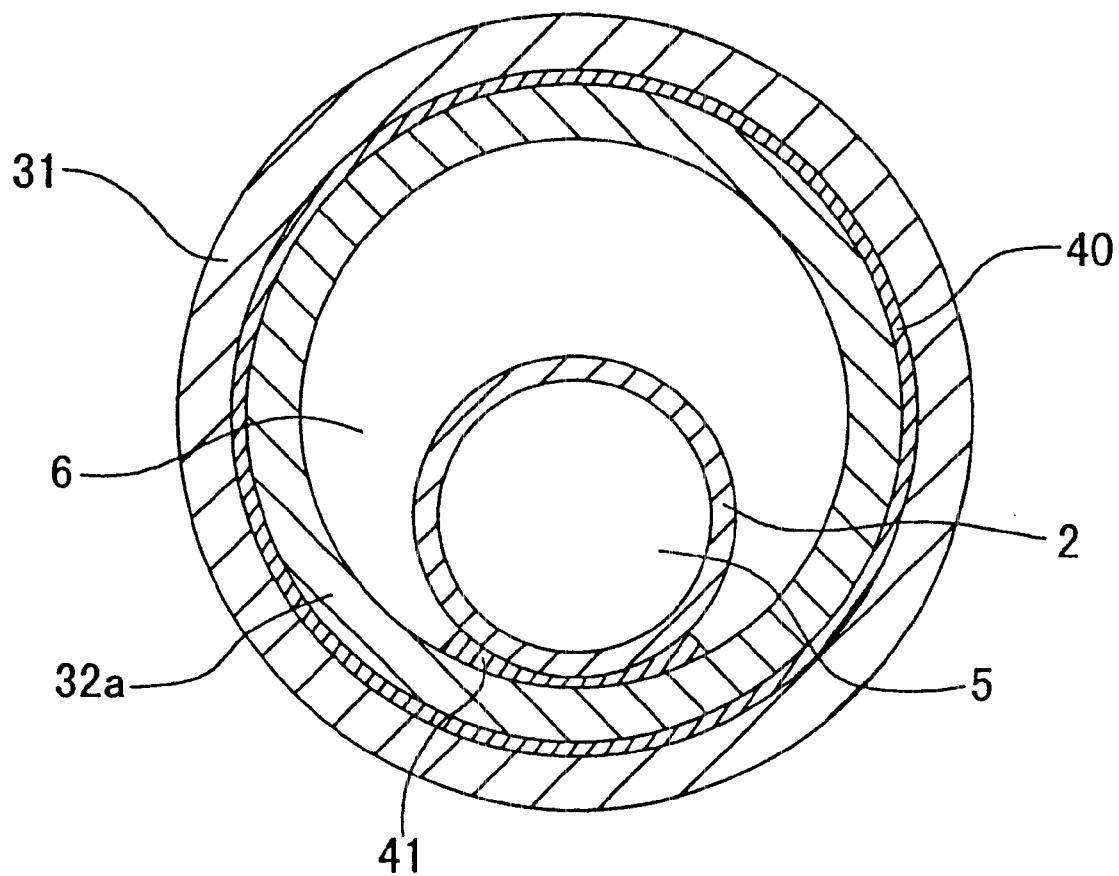
FIG. 4 is a sectional view taken along a line I—I of FIG. 2.

As shown in FIGS. 2 and 4, the front portion 32a of the rear-side tube 32 is joined with (fixed to) the rear end portion of the front-side tube 31 through an adhesive material 40. The rear-side tube 32 and the front-side tube 31 may be fixed to each other not with the adhesive material 40 but with a fit-in force applied thereto. If the material of the rear-side tube 32 and that of the front-side tube 31 are compatible with each other, both may be connected with each other (fixed to each other) by solvent bonding or fusing.

As shown in FIGS. 2 and 4, the inner surface of the front portion 32a of the rear-side tube 32 is joined with (fixed to) the inner tube 2 through an adhesive material 41. If the material of the inner tube 2 and that of the rear-side tube 32 are compatible with each other, both may be connected with each other (fixed to each other) by solvent bonding or fusing. It is preferable to treat the outer surface of the inner tube 2 and the inner surface of the front portion 32a of the rear-side tube 32 to fix both tubes 2, 32 to each other at a high degree. The diameter of the portion of connection between the front-side tube 31 and the rear-side tube 32 may be decreased to increase the connection surface thereof.

As shown in FIG. 4, only a part of the inner tube 2 in its circumferential direction is fixed to the outer tube 3 (rear-side tube 32), whereas the other parts of the inner tube 2 are unfixed to the outer tube 3 (front-side tube 31 and rear-side tube 32). In the unfixed part, the second lumen 6 is formed between the outer surface of the inner tube 2 and the inner surface of the outer tube 3. The inner tube 2 is fixed to the outer tube 3 (rear-side tube 32) at 5% 70% and more favorably, 20%–50% in the circumferential direction thereof. The inner tube 2 is only fixed to the outer tube 3 at the above fixed portion except a proximal end portion of the inner tube 2. In other words, the inner tube 2 is not fixed to the outer tube on the front side from the above fixed portion, the inner tube 2 is not fixed to the outer tube 3 on the rear side from the above fixed portion except the proximal end portion of the inner tube 2. The inner tube 2 is fixed to the outer tube 3 at the proximal end portion of the inner tube 2 by a branch hub 12.

As described above, in the blood vessel dilatation apparatus 1 of the present invention, the inner tube 2 and the outer tube 3 are fixed to each other at the rear part 3b having a large clearance between the outer surface of the inner tube 2 and the inner surface of the outer tube 3. Thus, the inner tube 2 can be prevented from being bent, curved or twisted inside the outer tube 3. Therefore, a pressing force generated at the rear portion of the blood vessel dilatation apparatus 1 is not absorbed by intermediate parts thereof but can be reliably transmitted to the front end thereof. Thus, the pushability (travel performance in blood vessel) of the blood vessel dilatation apparatus in a blood vessel is preferable. In addition, the flow of an operating fluid in the second lumen 6 between the inner tube 2 and the outer tube 3 is not prevented because the inner tube 2 is not bent, curved or twisted inside the outer tube 3. Thus, the operating fluid flows into the dilatation member 9 and is discharged therefrom favorably.

The length of the front-side tube 31 of the outer tube 3 is 50–2000 mm, and favorably, 100–500 mm. The outer diameter thereof is 0.5 mm–2 mm, and favorably, 0.8–1.5 mm in the region rearward from the diameter changing portion 31a. The outer diameter thereof is 0.3 mm–1.5 mm, and favorably, 0.5–1 mm in the region forward from the diameter changing portion 31a. The thickness thereof is 25–200 µm, and favorably 50–100 µm. The difference between the outer diameter of the inner tube 2 and the inner diameter of the front-side tube 31 is 0.05–0.50 mm, and favorably 0.1–0.40 mm. The diameter changing portion 31a (in other words, rear end of the front part 3a of the outer tube 3) is formed at a position corresponding to a position from which the blood vessel dilatation apparatus 1 can be inserted sufficiently into a peripheral blood vessel of a stenosis portion to be dilated. Thus, the diameter changing portion 31a is formed proximately to the front end (front end of the inner tube 2) of the blood vessel dilatation apparatus 1. More specifically, it is formed at a position 3–50 cm and favorably 5–30 cm rearward from the front end (front end of the inner tube 2) of the blood vessel dilatation apparatus 1.

The following materials can be preferably used to form the outer tube 3; polyolefin (for example, polyethylene, polypropylene, polybuthane, ethylene-propylene copolymer, ethylene-vinyl acetate copolymer, ionomer, and a mixture containing two or more of these polyolefins); crosslinked polyolefins; high polymer materials including polyvinyl chloride, polyamide, polyamide elastomer, polyester, polyester elastomer, polyurethane, polyurethane elastomer, fluoroplastics, silicone rubber, latex rubber, and the like; and mixtures of these high polymer materials.

It is preferable that the material to form the rear-side tube 32 has a higher degree of rigidity than that of the front-side tube 31. In other words, it is preferable to form the front-side tube 31 of a flexible material. The rear-side tube 32 is made of a high polymer material having a certain degree of flexibility or metal.

As the high polymer material, the following substances can be used: polyolefin (for example, polyethylene, polypropylene, ethylene-propylene copolymer, ionomer, and a mixture containing two or more thereof); crosslinked polyolefins; polyvinyl chloride, polyamide, polyamide elastomer, polyester, polyester elastomer, polyurethane, polyurethane elastomer, polyimide, fluoroplastics. The material of the rear-side tube 32 may be the same as that of the front-side tube 31. In this case, it is preferable that the rear-side tube 32 is made of a material having a higher rigidity (hardness) than the material of the front-side tube 31. If the material of the rear-side tube 32 is the same as that of the front-side tube 31, it is preferable that the front-side tube 31 is formed of a material having a high degree of plasticization (for example, material containing much plasticizer). If the front-side tube 31 is formed of a copolymerizate, it is preferable to use one having much soft segment.

As the material of the metal tube, the following metal and alloys can be used: stainless extensible alloys such as austenitic stainless steel (for example, SUS304, SUS316, SUS321, and the like) and maraging stainless, steel; metal such as super elastic metal (for example, super-elastic alloy); and alloys. The super-elastic alloy here refers to an alloy that is generally called a shape-memory alloy and exhibits super-elasticity at least at the body temperature (around 37° C.). Favorable super-elastic alloys include Ti—Ni alloy with 49–53 atom percent of Ni, Cu—Zn alloy with 38.5 to 41.5 wt % of Zn, Cu—Zn—X alloy with 1 to 10 wt % of X (X=Be, Si, Sn, Al, Ga), and Ni—Al alloy with 36–38 atom percent of Al. The Ti—Ni alloy is most favorable. The mechanical property of the Ti—Ni alloy can be altered as desired by replacing a part thereof with 0.01 to 10.0 atom percent of X to form Ti—Ni—X alloy (X=Co, Fe, Mn, Cr, V, Al, Nb, W, B, etc.), replacing a part of the Ti—Ni alloy with 0.01 to 30.0 atom percent of X to form Ti—Ni—X alloy (X=Cu, Pb, Zr) or selecting the condition of a reduction ratio of cold working and/or the condition of the final heat treatment. The super-elasticity here means the capacity of the super-elastic metal to return to its almost original shape at a temperature at which it is used after it is deformed (bent, elongated or compressed) to such a degree that ordinary metal undergoes permanent deformation.

The length of the rear-side tube 32 is 50–2000 mm; and favorably, 100–1700 mm. The outer diameter thereof is 0.5 mm–2 mm, and favorably, 0.8–1.1 mm. The thickness thereof is 25–200 µm, and favorably 50–100 µm. The length of the front portion 32a is 1–500 mm, and favorably, 3–300 mm. The outer diameter thereof is 0.1 mm–1.45 mm, and favorably, 0.4–1.05 mm. The thickness thereof is 25–200 µm. It is preferable that the inner diameter of the front portion 32a is greater than that of the front part 3a (region forward from the diameter changing portion 31a of the front-side tube 31) of the outer tube 3. Owing to the dimension of the rear-side tube 32 and that of the front portion 32a, it is possible to secure a wide cross-sectional area of the second lumen 6 in the fixing portion of the inner tube 2 and the outer tube 3 and allow the fluid to flow smoothly into the dilatation member 9 and to be discharged smoothly therefrom. But according to the present invention, the inner diameter of the front portion 32a may be equal to or a little smaller than that of the front part 3a.

Figure 15:
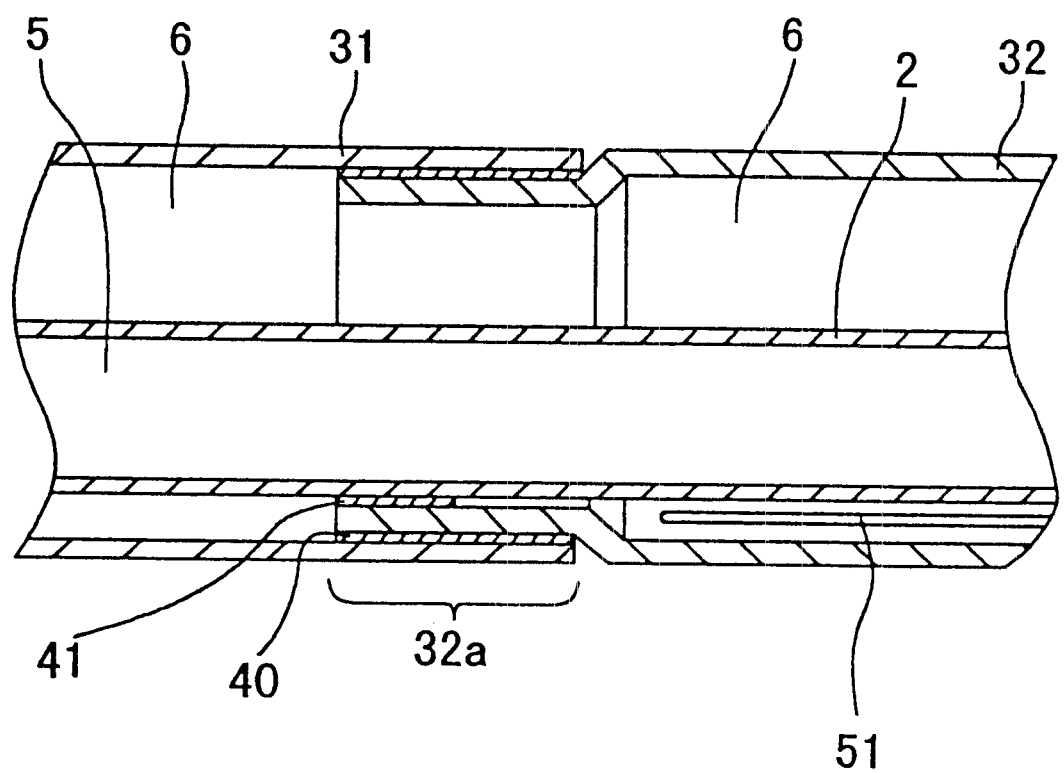
FIG. 15 is an enlarged vertical section showing the construction of a fixed portion of inner and outer tubes of still another embodiment of the blood vessel dilatation apparatus of the present invention.

The catheter may have a reinforcing member. A tip portion of the reinforcement member is located in the vicinity of the fixed portion of the inner tube and the outer tube and on a proximal side from the fixed portion. The catheter shown in FIG. 15 has a reinforcement wire 51 arranged between the inner tube 2 and the outer tube 3 (or lumen 6). A tip portion of the reinforcement wire may be located to vicinity the fixed portion of the inner tube and the outer tube and on a proximal side from the fixed portion. A tip portion of the reinforcement wire may be not fixed to the inner tube or the outer tube. A base end portion of the reinforcement wire may be fixed to the inner tube or the outer tube by a hub. The reinforcing member may be a pipe inserted between the inner tube and the outer tube (lumen 6). The reinforcing pipe may be fixed to the inner tube or the outer tube. The reinforcing member pipe may be has a spiral slit at a distal end portion thereof. A pitch of the slit may become gradually smaller toward the distal end.

The reinforcement member (wire or pipe) preferably consists of elastic metal such as stainless steel, super elastic alloy, Cu or Cu alloy, Ti or Ti alloy, precious metals or hard resin such as polyimide, polyamide, polyester (polyethylene-terephthalate, polybutylene-terephthalate, etc.), polyphenylenesulfide.

The outer surface of the front-side tube 31 and that of the rear-side tube 32 may be coated with resin having adaptability to human body and in particular anti-thrombus property. As the material having anti-thrombus property, it is preferable to use polyhydroxy ethyl methacrylate, copolymer of hydroxy ethyl methacrylate and styrene (for example, HEMA-St-HEMA block copolymer).

As the material of the adhesive materials 40,41, it is preferable to use adhesive agents such as cyanoacrylate adhesive agent, acrylic adhesive agent, epoxy adhesive agent, urethane adhesive agent, hot-melt adhesive agent, elastomer adhesive agent, thermoplastic adhesive agent, light vulcanize adhesive agent, ultraviolet vulcanize adhesive agent; and high polymer materials having adhesive property such as modified polyolefins (for example, ethylene-vinyl acetate copolymer, ethylene-methyl methacrylate copolymer, ethylene-ethyl acrylate copolymer, ethylene-methyl acrylate copolymer, ethylene-ethyl acrylate-maleic anhydride copolymer, ethylene-acrylic acid copolymer, ionomer, MAH-g-polyolefin).

In fixing the inner tube 2 and the outer tube 3 (rear-side tube) to each other, the adhesive material is interposed between the front end portion of the rear-side tube 32 and the inner tube 2 and heated to fuse both (weld) to each other or applied light or ultraviolet.

The rear-side tube 32 and the front-side tube 31 are fixed to each other with the adhesive material 40 in a length of 0.5–10 mm and favorably, 1–5 mm in the longitudinal direction of the inner tube 2 and the outer tube 3. The adhesive material 41 connecting the inner tube 2 and the outer tube 3 (rear-side tube 32) with each other is applied thereto in such an extent that the flexibility thereof at a connection portion does not deteriorate. More specifically, both are fixed to each other with the adhesive material 41 in a length of 0.5–30 mm and favorably, 1–5 mm in the longitudinal direction thereof.

Figure 7:
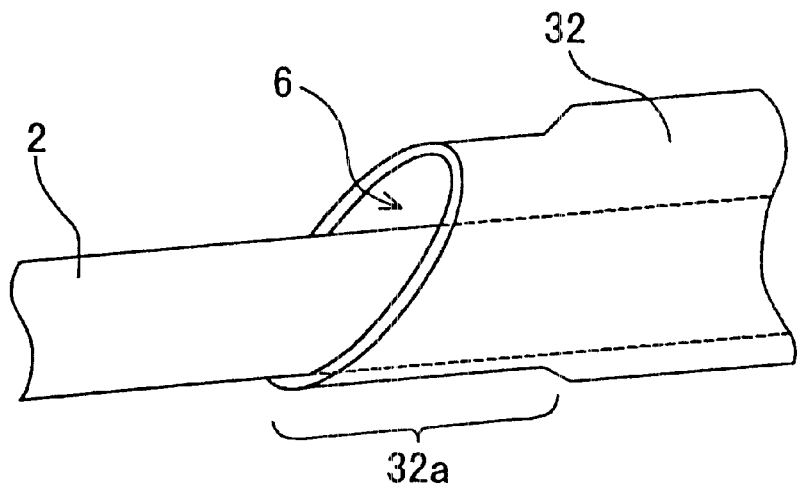
FIG. 7 is a perspective view showing another embodiment of the configuration of a front portion of a rear-side tube.
Figure 8:
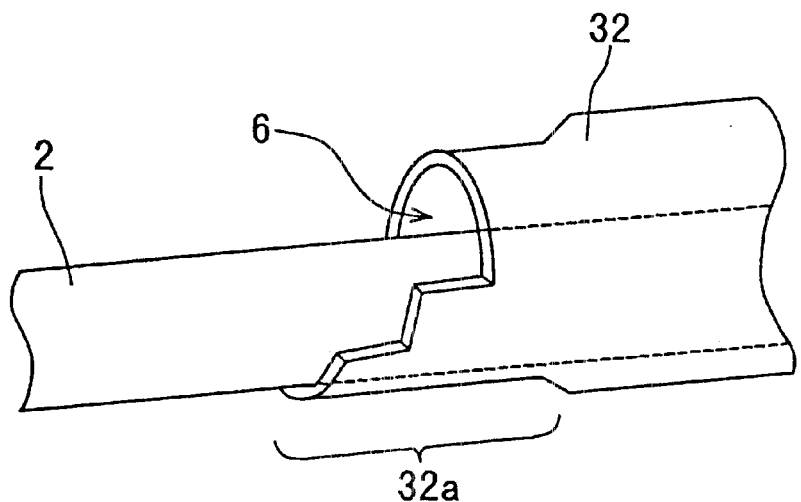
FIG. 8 is a perspective view showing still another embodiment of the configuration of a front portion of a rear-side tube.
Figure 9:
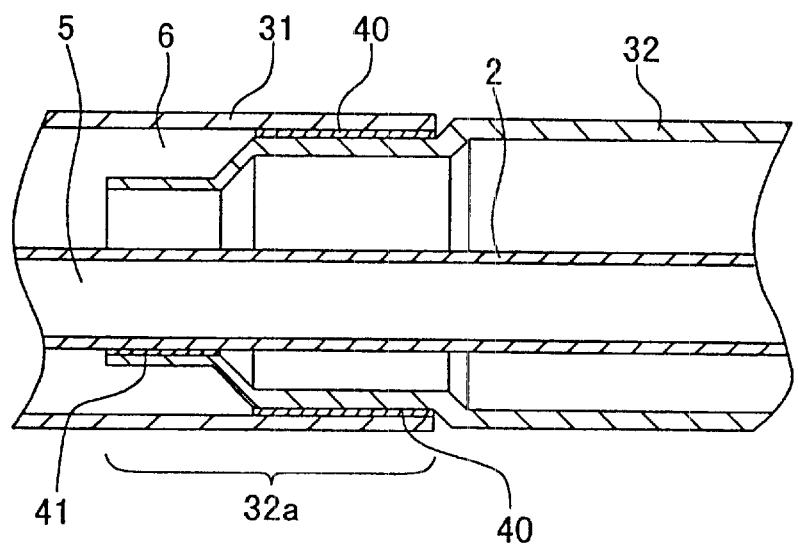
FIG. 9 is a perspective view showing a further embodiment of the configuration of a front portion of a rear-side tube.

The configuration of the front portion 32a of the rear-side tube 32 is not limited to the one shown in FIG. 2, but as shown in FIG. 7, may be open obliquely to the longitudinal direction of the blood vessel dilatation apparatus 1 or as shown in FIG. 8, the front end thereof may be stepped. Further, as shown in FIG. 9, it is possible to set the diameter of the front side of the front portion 32a smaller than the rear side thereof and fix the inner surface of the front side of the front portion 32a to a part of the inner tube 2 in its circumferential direction. In this case, the inner tube 2 and the outer tube 3 can be fixed to each other coaxially or approximately coaxially.

Figure 10:
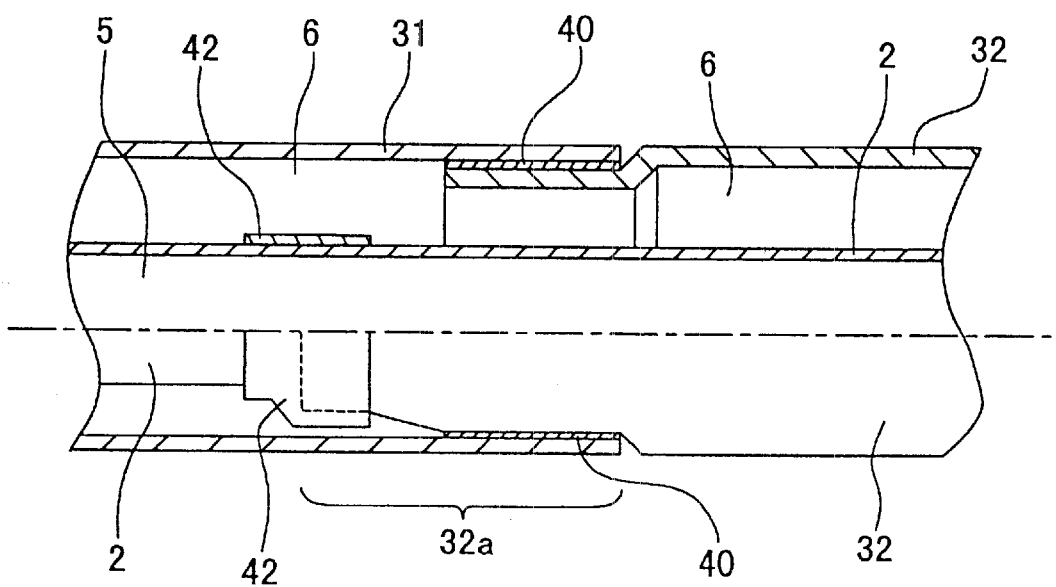
FIG. 10 is an enlarged vertical section showing the construction of a fixed portion of inner and outer tubes of another embodiment of the blood vessel dilatation apparatus of the present invention.
Figure 11:
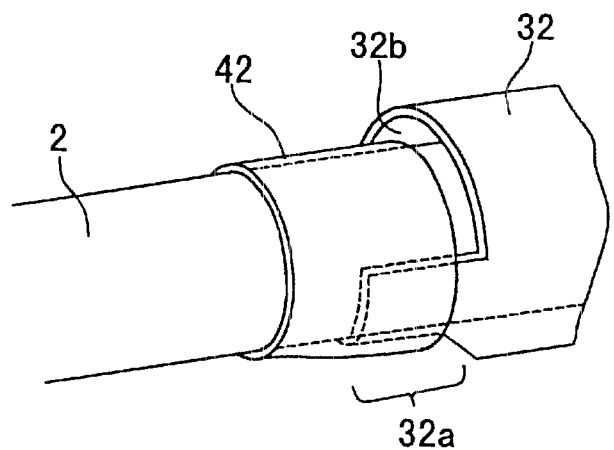
FIG. 11 is a perspective view showing the construction of the fixed portion of the inner and outer tubes of the embodiment shown in FIG. 10.

Regarding the construction of the portion connecting the inner tube 2 and the front-side tube 31 with each other and the inner tube 2 and the rear-side tube 32 with each other, as shown in FIGS. 10 and 11, the front side of the front portion 32a of the rear-side tube 32 is set smaller than the rear side of the front portion 32a in diameter, and the front side of the front portion 32a is cut off axially partly in the circumferential direction of the rear-side tube 32 to form a trough-shaped cut-out portion 32b (see FIG. 11) whose upper part is open. The cut-out front side of the front portion 32a is covered with a heat-shrinkable tube 42 to connect (fix) the inner tube 2 and the rear-side tube 32 to each other by thermal shrinkage of the heat-shrinkable tube 42. The heat-shrinkable tube 42 can be obtained by forming a tube of a drawable material such that its inner diameter is smaller than the outer diameter of the inner tube 2 and expanding it radially. As the material of the heat-shrinkable tube 42, polyolefin such as polyethylene, polypropylene; and EAA (ethylene-vinyl acetate copolymer) can be used. Heated air is applied to the heat-shrinkable tube 42, with the heat-shrinkable tube 42 covering the diameter changing front end of the front portion 32a of the front-side tube 32. As a result, the heat-shrinkable tube 42 contracts. and contacts the front portion 32a of the front-side tube 32 and the outer surface of a part of the inner tube 2 proximate thereto. In this manner, the outer tube 3 can be fixed to the inner tube 2.

Figure 12:
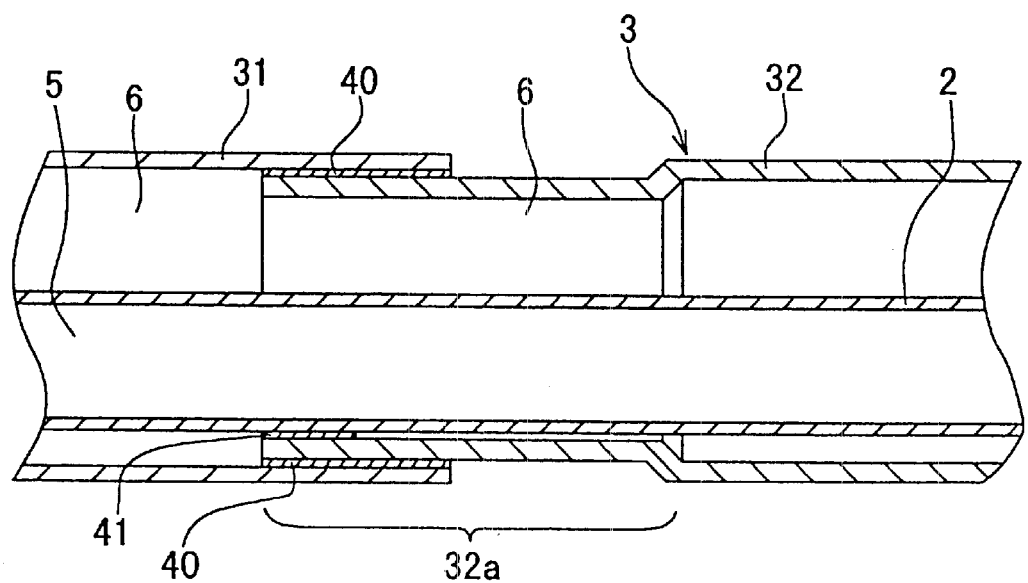
FIG. 12 is an enlarged vertical section showing the construction of a fixed portion of inner and outer tubes of another embodiment of the blood vessel dilatation apparatus of the present invention shown in FIG. 1.

Regarding another construction of the portion of connection between the inner tube 2 and the front-side tube 31 as well as the rear-side tube 32, as shown in FIG. 12, the front portion 32a of the rear-side tube 32 is set longer than the one shown in FIG. 2. The front portion of the front portion 32a is connected (fixed) to the rear portion of the front-side tube 31.

The front part of the second lumen 6 formed between the outer surface of the inner tube 2 and the inner surface of the outer tube 3 communicates with the interior of the dilatation member 9. The rear part of the second lumen 6 communicates with the second opening 11 of the branch hub 12 forming an injection port for injecting the fluid (for example, angiographic agent) that is used to expand the dilatation member 9.

The dilatation member 9 is contractible or foldable. In an unexpanded state, it can be folded on the periphery of the inner tube 2. As shown in FIG. 5, a part of the dilatation member 9 is formed as an approximately cylindrical portion 9c having the same diameter to easily expand the stenosis portion of a blood vessel. The cylindrical portion 9c is foldable. The cylindrical portion 9c may be polygonal prism-shaped. The rear portion of the dilatation member 9 is liquid-tightly bonded to the front portion of the outer tube 3 with an adhesive agent or fused thereto. The front portion 9a is also liquid-tightly bonded to the front portion of the inner tube 2 with an adhesive agent or fused thereto. As shown in FIG. 5, the dilatation member 9 forms a dilatation space 15 between the inner surface of the dilatation member 9 and the outer surface of the inner tube 2. The rear portion of the dilatation space 15 communicates with the second lumen 6 in its entire periphery. Because the rear portion of the dilatation space 15 communicates with the second lumen 6 having a comparatively large cross[0ax3]ectional area, it is easy to inject a fluid into the dilatation member 9 from the second lumen 6 to expand the dilatation member 9.

The dilatation member 9 is tapered in the region between the front portion 9a at which the dilatation member 9 and the inner tube 2 are fixed to each other and the rear portion 9b at which the dilatation member 9 and the outer tube 3 are fixed to each other. Regarding the size of the dilatation member 9, when the dilatation member 9 is dilated, the outer diameter of the cylindrical portion 9c thereof is 1.0–10 mm, and favorably 1.0–5.0 mm; the length thereof is 5–50 mm, and favorably 10–40 mm; and the entire length of the dilatation member 9 is 10–70 mm, and favorably 15–60 mm.

Materials having a certain degree of flexibility can be preferably used to form the dilatation member 9; polyolefin (for example, polyethylene, polypropylene, polybuthane, ethylene-propylene copolymer, ethylene-vinyl acetate copolymer, ionomer, and a mixture containing two or more thereof); crosslinked polyolefins; polyester such as polyethylene terephthalate; high polymer materials including polyvinyl chloride, polyurethane, polyphenylene sulfide, polyamide, polyamide elastomer, fluoroplastics; and silicone rubber, latex rubber, and the like.

As shown in FIG. 5, it is preferable to install a marker 14 made of an X-ray-nonpermeable material on a portion, of the outer surface of the inner tube 2, positioned at the center of the cylindrical portion 9c of the dilatation member 9. It is preferable to form the markers 14 made of a coil spring or a ring. It is preferable to use a material having a high degree of radiopaque performance, for example, Pt, Pt alloy, W, W alloy, Ag, and Ag alloy as the material of the markers 14. As shown in FIG. 5, the marker 14 is secured on the outer surface of the inner tube 2 at two positions: One is located at a sition corresponding to the center of the cylindrical portion 9c and the other is located at a position corresponding to the rear portion thereof. The installation position of the marker 14 is not limited to that shown in FIG. 5, but it may be secured at a position, of the outer surface of the inner tube 2, corresponding to the center of the cylindrical portion 9c or at a position, of the outer surface of the inner tube 2, corresponding to both ends of the cylindrical portion 9c.

To facilitate the insertion of the blood vessel dilatation apparatus 1 into a blood vessel and a guide catheter, it is preferable to treat the outer surface of the outer tube 3 (outer surface of front-side tube 31 and/or outer surface of rear-side tube 32) and that of the dilatation member 9 to allow them to be lubricant when they contact blood or the like. It is preferable to coat the outer surface of the outer tube 3 and the dilatation member 9 with hydrophilic polymers such as poly (2-hydroxy ethyl methacrylate), polyhydroxy ethyl acrylate, hydroxy propyl cellulose, methyl vinyl ether maleic anhydride copolymer, polyethylene glycol, polyacrylamide, polyvinyl pyrrolidone or fix these polymers thereto.

Figure 6:
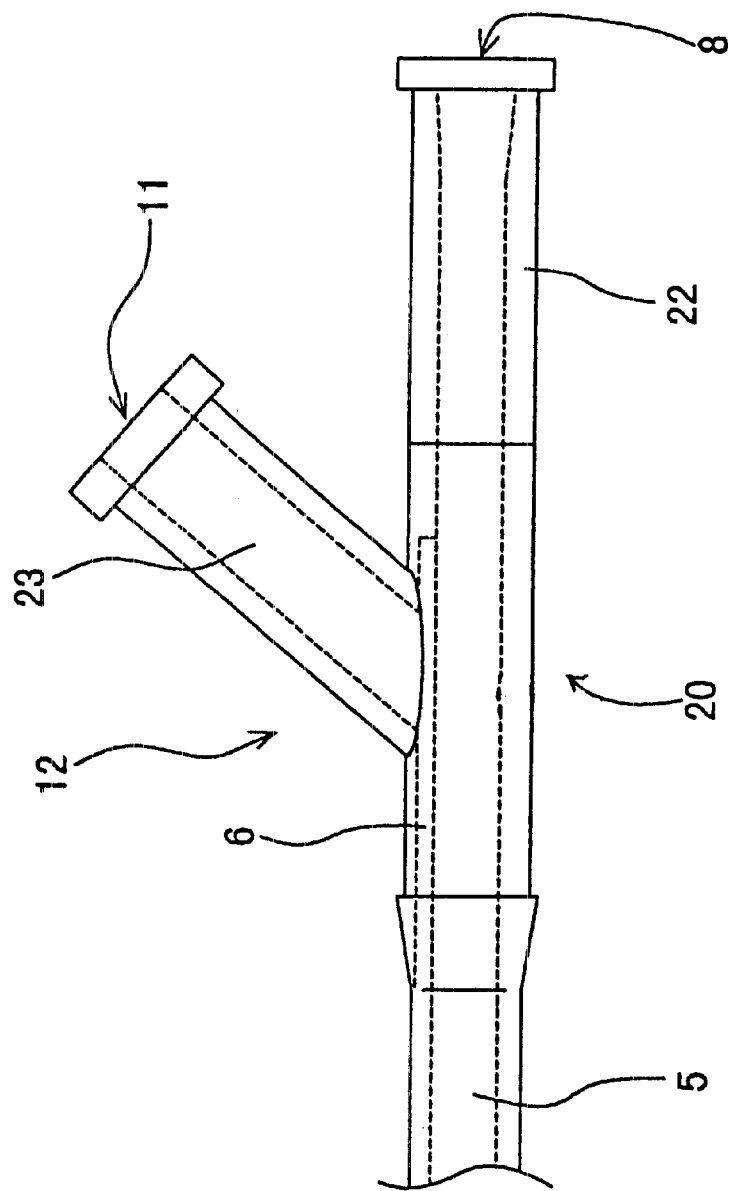
FIG. 6 is an enlarged external appearance view showing a rear part of the blood vessel dilatation apparatus shown in FIG. 1.

As shown in FIG. 6, the branch hub 12 has a first opening 8 communicating with the first lumen 5 and forming the guide wire port and a second opening 11 communicating with the second lumen 6 and forming the injection port. The branch hub 12 includes an inner tube hub 22 fixed to the inner tube 2 and an outer tube hub 23 fixed to the outer tube 3 (rear-side tube 32). The outer tube hub 23 and the inner tube hub 22 are fixed to each other. It is preferable to use the following thermoplastic resin to form the branch hub 12: polycarbonate, polyamide, polysulfone, polyarylate, methacrylate-butylene-styrene copolymer, and the like.

The blood vessel dilatation apparatus 20 shown in FIG. 13 will be described below. The construction of a blood vessel dilatation apparatus 10 is fundamentally the same as that of the blood vessel dilatation apparatus 1. As described previously, in the blood vessel dilatation apparatus 1, the outer tube 3 includes the front-side tube 31 and the rear-side tube 32 fixed to the front-side tube 31; the front portion 32a of the rear-side tube 32 is connected with the inner surface of the rear end portion of the front-side tube 31; and the front portion 32a of the rear-side tube 32 is connected with the inner tube 2 through the inner surface thereof. The blood vessel dilatation apparatus 20 of the embodiment is different from the blood vessel dilatation apparatus 1 as described below: The outer tube 3 includes the front-side tube 31 and the rear-side tube 32 fixed thereto; the front portion of the rear-side tube 32 is connected with the outer surface of the rear portion 31b of the front-side tube 31; and the inner surface of the rear portion 31b of the front-side tube 31 is connected with the inner tube 2.

The rear-side tube 32 has substantially the same outer diameter over its whole length. As shown in FIG. 13, the outer and inner diameters of the rear portion 31b of the front-side tube 31 are smaller than those of the front portion of the front-side tube 31 in the region, rearward from the diameter changing portion 31a. The outer diameter of the rear portion 31b is almost equal to the inner diameter of the front portion of the rear-side tube 32. The inner diameter of the rear-side tube 32 and the inner diameter of the front-side tube 31 in the region rearward from the diameter changing portion 31a are formed larger than the inner diameter of the front part 3a (the part of the outer tube 3 forward from the diameter changing portion 31a of the front-side tube 31), excluding the rear portion 31b.

The rear portion 31b of the front-side tube 31 is fixed to the inner surface of the front portion of the rear-side tube 32 through the adhesive material 40. The front-side tube 31 and the rear-side tube 32 may be fixed to each other not with the adhesive material 40 but with a fit-in force applied thereto. If the material of the rear-side tube 32 and that of the front-side tube 31 are compatible with each other, both may be connected with each other (fixed to each other) by solvent bonding or fusing.

The inner surface of the rear portion 31b of the front-side tube 31 and the inner tube 2 are fixed to each other through the adhesive material 41. If the material of the inner tube 2 and that of the front-side tube 31 are compatible with each other, both may be fixed to each other by solvent bonding or fusing. It is preferable to treat the outer surface of the inner tube 2 and the inner surface of the rear portion 31b of the front-side tube 31 to fix both to each other at a high degree. The diameter of the portion of connection between the front-side tube 31 and the rear-side tube 32 may be longitudinally decreased to increase the connection surface thereof.

It is preferable that in the embodiment, the inner diameter of the rear portion 31b of the front-side tube 31 is greater than that of the front part 3a (region forward from the diameter changing portion 31a of the front-side tube 31) of the outer tube 3. But the inner diameter of the rear portion 31b of the front-side tube 31 may be equal to or a little smaller than that of the front part 3a.

In the blood vessel dilatation apparatus 20 of the present invention, the inner tube 2 and the outer tube 3 are fixed to each other at the rear part 3b having a large clearance between the outer surface of the inner tube 2 and the inner surface of the outer tube 3. Thus, the inner tube 2 can be prevented from being bent, curved or twisted inside the outer tube 3. Therefore, a pressing force generated at the rear portion of the blood vessel dilatation apparatus 20 is not absorbed by intermediate parts thereof but can be reliably transmitted to the front end thereof. Thus, the pushability (travel performance in blood vessel) of the blood vessel dilatation apparatus 20 in a blood vessel is preferable. In addition, the flow of an operating fluid in the second lumen 6 between the inner tube 2 and the outer tube 3 is not prevented because the inner tube 2 is not bent, curved or twisted inside the outer tube 3. Thus, the operating fluid flows into the dilatation member 9 and is discharged therefrom favorably.

Except the configuration of the front portion of the rear-side tube 32, that of the rear portion 31b of the front-side tube 31, and the method of connection between the rear-side tube 32 and the front-side tube 31, the construction of the blood vessel dilatation apparatus 20 is the same as that of the blood vessel dilatation apparatus 1. That is, the material of each of the front-side tube 31, the rear-side tube 32, the adhesive materials 40, 41; the dimension of each of the front-side tube 31 and the rear-side tube 32; and the bonding length of each of the adhesive materials 40, 41 of the blood vessel dilatation apparatus 20 are the same as those of the blood vessel dilatation apparatus 1.

The blood vessel dilatation apparatus 10 shown in FIG. 14 will be described below. The construction of a blood vessel dilatation apparatus 10 is fundamentally the same as that of the blood vessel dilatation apparatus 1 shown in FIGS. 1 through 12. As described previously, in the blood vessel dilatation apparatus 1, the outer tube 3 includes the front-side tube 31 and the rear-side tube 32 fixed to the front-side tube 31; the front portion 32a of the rear-side tube 32 is connected with the inner surface of the rear end portion of the front-side tube 31; and the front portion 32a of the rear-side tube 32 is connected with the inner tube 2 through the inner surface thereof. The blood vessel dilatation apparatus 10 of the embodiment is different from the blood vessel dilatation apparatus 1 as described below: The outer tube 3 includes the front-side tube 31; the rear-side tube 32; a connection tube 33 disposed inside the front-side tube 31 and the rear-side tube 32 and connected with the rear portion 31b of the front-side tube 31 and the front portion 32a of the rear-side tube 32; and the connection tube 33 is connected (fixed) to the inner tube 2 through the inner surface thereof.

The connection tube 33 is cylindrical. The front portion thereof is in penetration into the rear portion 31b of the front-side tube 31, and the rear portion thereof is in penetration into the front portion 32a of the rear-side tube 32. The outer diameter of the front portion of the connection tube 33 is almost the same as the inner diameter of the rear portion 31b of the front side tube 31. The outer diameter of the rear portion of the connection tube 33 is almost the same as the inner diameter of the front portion 32a of the rear-side tube 32. The length of the connection tube 33 is favorably 6–60 mm and more favorably 10–30 mm.

The inner diameter of the rear part 3b of the outer tube 3 (inner diameter of the rear-side tube 32 and the part of the outer tube 3 rearward from the diameter changing portion 31a of the front-side tube 31) is formed larger than the inner diameter of the front part 3a in most of the part thereof except at least the region in which the connection tube is present. It is preferable that the inner diameter of the connection tube 33 which is a part of the outer tube 33 is formed larger than, the inner diameter of the front part 3a of the outer tube 3 (the part of the outer tube 3 forward from the diameter changing portion 31a of the front-side tube 31). But according to the present invention, the inner diameter of the connection tube 33 may be equal to or a little smaller than that of the front part 3a.

The outer surface of the front portion of the connection tube 33 and the inner surface of the rear portion 31b of the front-side tube 31 are bonded to each other with an adhesive material 43. Similarly, the outer surface of the rear portion of the connection tube 33 and the inner surface of the front portion 32a of the rear-side tube 32 are bonded to each other with an adhesive material 44. The outer surface of the connection tube 33 may be bonded to the front-side tube 31 and the rear-side tube 32. If the mate rial of the connection tube 33, that of the rear-side tube 32, and that of the front-side tube 31 are compatible with one another, they may be connected with one another (fixed to each other) by fusing. In this manner, the rear-side tube 32 and the front-side tube 31 are fluid-tightly connected with each other through the connection tube 33.

The connection tube 33 may be formed of the same material as that of the front-side tube 31 and that of the rear-side tube 32.

Figure 14:
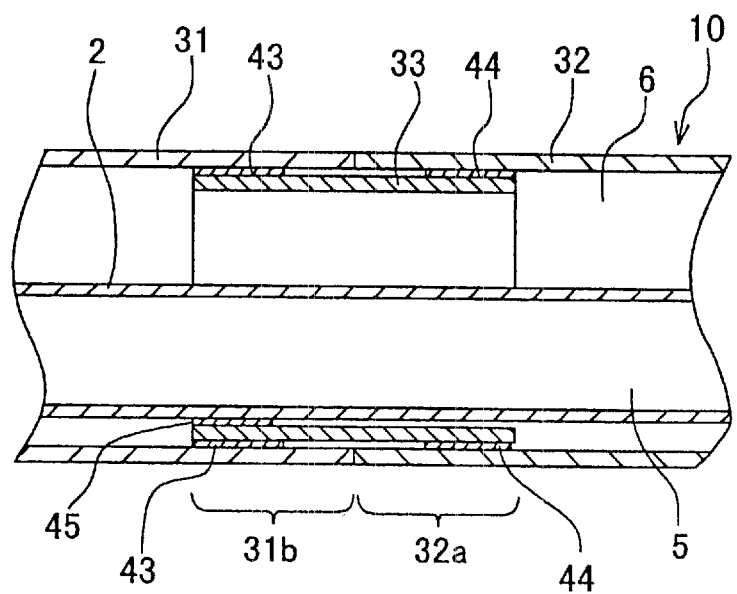
FIG. 14 is an enlarged vertical section showing the construction of a fixed portion of inner and outer tubes of still another embodiment of the blood vessel dilatation apparatus of the present invention.

In the example shown in FIG. 14, the inner surface of the front portion of the connection tube 33 and the outer surface of the inner tube 2 are connected (fixed) to each other through an adhesive material 45. But the inner surface of the rear portion of the connection tube 33 and the inner tube 2 may be connected (fixed) to each other through the adhesive material 45. If the material of the inner tube 2 and that of the rear-side tube 32 or the material of the inner tube 2 and that of the front-side tube 31 are compatible with each other, both may be fixed to each other by solvent bonding or fusing. It is preferable to treat the outer surface of the inner tube 2 and the inner surface of the rear portion of the front-side tube 31 to fix both tubes 2, 31 to each other at a high degree. The diameter of the portion of connection between the front-side tube 31 or the rear-side tube 32 and the inner tube 2 may be decreased longitudinally to increase the connection surface thereof.

The adhesive materials 43, 44, and 45 may be formed of the same material as that of the adhesive materials 40, 41.

In the blood vessel dilatation apparatus 10 of the present invention, the inner tube 2 and the outer tube 3 are fixed to each other at the rear part 3b having a large clearance between the outer surface of the inner tube 2 and the inner surface of the outer tube 3. Thus, the inner tube 2 can be prevented from being bent, curved or twisted inside the outer tube 3. Therefore, a pressing force generated at the rear portion of the blood vessel dilatation apparatus 10 is not absorbed by intermediate parts-thereof but can be reliably transmitted to the front end thereof. Thus, the pushability (travel performance in blood vessel) of the blood vessel dilatation apparatus 10 in a blood vessel is preferable. In addition, the flow of an operating fluid in the second lumen 6 between the inner tube 2 and the outer tube 3 is not prevented because the inner tube 2 is not bent, curved or twisted inside the outer tube 3. Thus, the operating fluid flows into the dilatation member 9 and is discharged therefrom favorably.

The connection tube 33 and the inner tube 2 are fixed to each other with the adhesive material 45 in a length of 0.5–30 mm and favorably, 1–10 mm in the longitudinal direction of the inner tube 2 and the connection tube 33. The adhesive material 45 is applied to connection tube 33 and the inner tube 2 in such an extent that the flexibility thereof at the bonding portion does not deteriorate.

Except the configuration of the front portion 32a of the rear-side tube 32, that of the -rear portion 31b of the front-side tube 31, and the method of the connection between the rear-side tube 32 and the front-side tube 31, the construction of the blood vessel dilatation apparatus 10 is the same as that of the blood vessel dilatation apparatus 1. That is, the material of each of the front-side tube 31, the rear-side tube 32; the dimension of each of the front-side tube 31 and the rear-side tube 32; and the like are the same as those of the blood vessel dilatation apparatus 1.

In the embodiment, it is possible to use a one-piece (having no joint) tube as the outer tube and disposing the connection tube inside the one-piece tube instead of the outer tube formed by connecting the front-side tube and the rear-side tube with each other.

Figure 13:
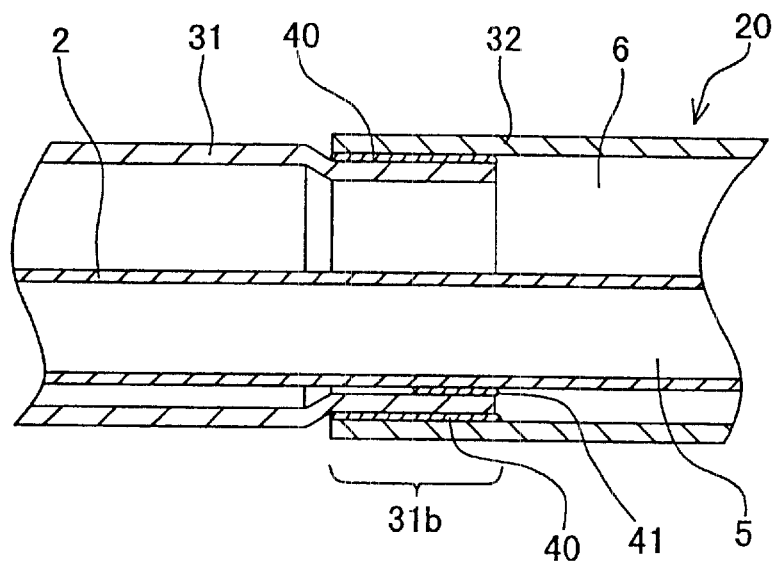
FIG. 13 is an enlarged vertical section showing the construction of a fixed portion of inner and outer tubes of another embodiment of the blood vessel dilatation apparatus of the present invention.

In the embodiment shown in FIGS. 1 through 12, the embodiment shown in FIG. 13, and the embodiment shown in FIG. 14, the diameter changing portion of the outer tube 3 is formed on the front-side tube 31. But the blood vessel dilatation apparatus of the present invention is not limited to this construction. The diameter changing portion of the outer tube 3 is formed on the rear-side tube 32.

According to the blood vessel dilatation apparatus of the present invention, the inner tube and the outer tube are fixed to each other at the rear part having a large clearance between the outer surface of the inner tube and the inner surface of the outer tube. Thus, the inner tube can be prevented from being bent, curved or twisted inside the outer tube. Therefore, a pressing force generated at the rear portion of the blood vessel dilatation apparatus is not absorbed by intermediate parts thereof but can be reliably transmitted to the front end thereof. Thus, the pushability (travel performance in blood vessel) of the blood vessel dilatation apparatus in a blood vessel is preferable. In addition, the flow of an operating fluid in the second lumen between the inner tube and the outer tube is not prevented because the inner tube is not bent, curved or twisted inside the outer tube. Thus, the operating fluid flows into the dilatation member and is discharged therefrom favorably.

What is claimed is:

1. A blood vessel dilatation apparatus comprising:
   an inner tube having a first lumen whose distal end is open, said inner tube having a front end;
   an outer tube coaxial with said inner tube, having a front end at a position rearward a predetermined length from said front end of said inner tube, and forming a second lumen between said outer tube and an outer surface of said inner tube;
   a dilatation member contractible or foldable, having a front end portion secured to said inner tube and a rear end portion secured to said outer tube and communicating with said second lumen in the vicinity of a rear end thereof;

a first opening provided at a rear end portion of said inner tube and communicating with said first lumen; and a second opening provided at a rear end portion of said outer tube and communicating with said second lumen, wherein said outer tube has a front part having a comparatively small diameter relative to another portion of the outer tube and extending rearward a predetermined length from a position at which said outer tube and said dilatation member are connected with each other; and a rear part located rearward of said front part and having an inner diameter greater than that of said front part at least in a greater part thereof; and said outer tube is fixed to said inner tube through an inner surface of said rear part at a front end portion of said rear part of said outer tube.

2. A blood vessel dilatation apparatus according to claim 1, wherein said apparatus has a fixed portion fixing said inner tube to the outer tube, said inner tube is not fixed to the outer tube on a front side from the fixed portion, and said inner tube is not fixed to said outer tube on a rear side from the fixed portion except at a proximal end portion of the inner tube.

3. A blood vessel dilatation apparatus according to claim 2, wherein said outer tube has a taper portion, said fixed portion being located on a rear side from said taper portions.

4. A blood vessel dilatation apparatus according to claim 1, wherein said outer tube includes a front-side tube and a rear-side tube fixed to said front-side tube; a front portion of said rear-side tube is connected with an inner surface of a rear end portion of said front-side tube; and a front portion of said rear-side tube is fixed to said inner tube through an inner surface thereof.

5. A blood vessel dilatation apparatus according to claim 1, wherein said outer tube includes a front-side tube and a rear-side tube fixed to said front-side tube; a front portion of said rear-side tube is connected with an outer surface of a rear end portion of said front-side tube; and a rear portion of said front-side tube is fixed to said inner tube though an inner surface thereof.

6. A blood vessel dilatation apparatus according to claim 1, wherein said outer tube includes a front-side tube; a rear-side tube; a connection tube disposed inside said front-side tube and said rear-side tube and fixed to a rear portion of said front-side tube and a front portion of said rear-side tube; and said connection tube is fixed to an inner tube through an inner surface thereof.

7. A blood vessel dilatation apparatus according to claim 1, wherein said inner tube is fixed to the outer tube at a proximal end portion of the inner tube by a hub.

8. A blood vessel dilatation apparatus according to claim 1, wherein said outer tube has a taper portion provided at a position rearward in a predetermined length from said front end of said inner tube.

9. A blood vessel dilatation apparatus according to claim 1, wherein said outer tube has a diameter changing portion forming a rear end of said front part, and said diameter changing portion is located at a position 3–50 cm rearward from a front end of said blood vessel dilatation apparatus.

10. A blood vessel dilatation apparatus according to claim 1, wherein said outer tube has a diameter changing portion forming a rear end of said front part, and said diameter changing portion is formed at a position 5–30 cm rearward from a front end of said blood vessel dilatation apparatus.

11. A blood vessel dilatation apparatus comprising:

an inner tube having a first lumen possessing an open distal end, the inner tube possessing a front end;

an outer tube coaxial with said inner tube, said outer tube having a front end at a position rearward a predetermined distance from said front end of said inner tube, and forming a second lumen between said outer tube and an outer surface of said inner tube;

a contractible or foldable dilatation member having a front end portion secured to said inner tube and a rear end portion secured to said outer tube and communicating with said second lumen in the vicinity of a rear end thereof;

a first opening provided at a rear end portion of said inner tube and communicating with said first lumen;

a second opening provided at a rear end portion of said outer tube and communicating with said second lumen;

said outer tube including a front part having a comparatively small diameter relative to another part of the outer tube and extending rearward over a predetermined length from a position at which said outer tube and said dilatation member are connected with each other, and a rear part having an inner diameter greater than that of said front part at least over a greater part of the rear part, and said outer tube including a front-side tube and a rear-side tube, said front-side tube having front and rear ends and a diameter changing portion located between the front and rear ends of the front-side tube, the rear-side tube having a front end portion and the front-side tube having a rear end portion, the front end portion of the rear-side tube being connected with an inner surface of the rear end portion of said front-side tube to fix the rear-side tube to the front-side tube, said front part of said outer tube being constructed by a portion of the front-side tube from the front end of the front-side tube to the diameter changing portion of the front-side tube, said rear part of said outer tube being constructed by a portion of the front-side tube from the diameter changing portion of the front-side tube to the rear end of the front-side tube and the rear-side tube, the front end portion of said rear-side tube having an inner surface fixed to said inner tube.

12. A blood vessel dilatation apparatus according to claim 11, wherein said inner tube is fixed to the outer tube at a fixed portion, and wherein said inner tube is not fixed to the outer tube on a front side from the fixed portion, and said inner tube is not fixed to said outer tube on a rear side from the fixed portion except at a proximal end portion of the inner tube.

13. A blood vessel dilatation apparatus according to claim 11, wherein said inner tube is fixed to the outer tube at a proximal end portion of the inner tube by a hub.

14. A blood vessel dilatation apparatus according to claim 11, wherein said diameter changing portion is a taper portion provided at a position rearward a predetermined distance from said front end of said inner tube.

15. A blood vessel dilatation apparatus comprising:

an inner tube having a first lumen whose distal end is open, said inner tube having a front end;

an outer tube coaxial with said inner tube, having a front end at a position rearward a predetermined distance from said front end of said inner tube, and forming a second lumen between said outer tube and an outer surface of said inner tube;

a contractible or foldable dilatation member having a front end portion secured to said inner tube and a rear end portion secured to said outer tube and communicating with said second lumen in the vicinity of a rear end thereof;

a first opening provided at a rear end portion of said inner tube and communicating with said first lumen, a second opening provided at a rear end portion of said outer tube and communicating with said second lumen, said outer tube having a front part possessing a comparatively small diameter relative to another part of said outer tube and extending rearward over a predetermined length from a position at which said outer tube and said dilatation member are connected with each other, said outer tube having a rear part possessing an inner diameter greater than that of said front part at least over a greater part of the rear part of the outer tube, and said outer tube including a front-side tube and a rear-side tube, the front-side tube having front and rear ends and a diameter changing portion located between the front and rear ends of the front-side tube, said rear-side tube having a front portion connected with an outer surface of a rear end portion of said front-side tube to fix the front-side tube to the rear-side tube, said front part of said outer tube being constructed by a portion of the front-side tube from the front end of the front-side tube to the diameter changing portion of the front-side tube, said rear part of said outer tube being constructed by a portion of the front-side tube from the diameter changing portion of the front-side tube to the rear end of the front-side tube and the rear-side tube, and the rear end portion of said front-side tube having an inner surface that is fixed to said inner tube.

16. A blood vessel dilatation apparatus according to claim 15, wherein said inner tube is fixed to the outer tube at a proximal end portion of the inner tube by a hub.

17. A blood vessel dilatation apparatus according to claim 16, wherein said diameter changing portion is a taper portion provided at a position rearward a predetermined distance from said front end of said inner tube.

18. A blood vessel dilatation apparatus according to claim 15, wherein said inner tube is fixed to the outer tube at a fixed portion, wherein said inner tube is not fixed to the outer tube on a front side from the fixed portion, and said inner tube is not fixed to said outer tube on a rear side from the fixed portion except at a proximal end portion of the inner tube.

19. A blood vessel dilatation apparatus comprising:

an inner tube having a first lumen whose distal end is open, the inner tube having a front end;

an outer tube coaxial with said inner tube, having a front end at a position rearward a predetermined distance from said front end of said inner tube, and forming a second lumen between said outer tube and an outer surface of said inner tube;

a contractible or foldable dilatation member having a front end portion secured to said inner tube and a rear end portion secured to said outer tube and communicating with said second lumen in the vicinity of a rear end thereof;

a first opening provided at a rear end portion of said inner tube and communicating with said first lumen;

a second opening provided at a rear end portion of said outer tube and communicating with said second lumen, said outer tube having a front part possessing a comparatively small diameter relative to another part of the outer tube and extending rearward over a predetermined length from a position at which said outer tube and said dilatation member are connected with each other, and a rear part possessing an inner diameter greater than that of said front part at least in a greater part of the rear part of the outer tube, said rear part possessing an inner surface that is fixed to said inner tube; and said outer tube including a front-side tube and a rear-side tube, the front-side tube having front and rear ends and a diameter changing portion located between the front and rear ends of the front-side tube, a connection tube disposed inside said front-side tube and said rear-side tube and fixed to a rear portion of said front-side tube and a front portion of said rear-side tube, said connection tube having an inner surface, and the connection tube being fixed to the inner tube through the inner surface of the connection tube.

20. A blood vessel dilatation apparatus according to claim 19, wherein the inner tube is fixed to the outer tube at a fixed portion, wherein said inner tube is not fixed to the outer tube on a front side from the fixed portion, and said inner tube is not fixed to said outer tube on a rear side from the fixed portion except at a proximal end portion of the inner-tube.

21. A blood vessel dilatation apparatus according to claim 19, wherein said inner tube is fixed to the outer tube at a proximal end portion of the inner tube by a hub.

22. A blood vessel dilatation apparatus according to claim 19, wherein said diameter changing portion is a taper portion provided at a position rearward a predetermined distance from said front end of said inner tube.

* * * * *

UNITED STATES PATENT AND TRADEMARK OFFICE
CERTIFICATE OF CORRECTION

PATENT NO. : 6,447,479 B1
DATED : September 10, 2002
INVENTOR(S) : Masakiyo Nobuyoshi et al.

It is certified that error appears in the above-identified patent and that said Letters Patent is hereby corrected as shown below:

Column 4,
Line 58, "tapes" is changed to -- taper --.

Column 10,
Line 24, "cross[Oax3]ectional" is changed to -- cross-sectional --.

Column 15,
Line 28, "portions" is changed to -- portion --.
Line 42, "though" is changed to -- through --.

Signed and Sealed this

Twenty-fifth Day of March, 2003

JAMES E. ROGAN
*Director of the United States Patent and Trademark Office*